United States Patent [19]

Okumura

[11] 4,234,799

[45] Nov. 18, 1980

[54] METHOD AND INSTRUMENT FOR PHOTOMETRIC ANALYSIS OF LIQUID USING CENTRIFUGE ROTOR

[75] Inventor: Akira Okumura, Takarazuka, Japan

[73] Assignees: Tetsuo Matsumoto, Hyogo; Eiko Okumura, Takarazuka; Hitachi Koki Company, Limited, Tokyo, all of Japan

[21] Appl. No.: 968,722

[22] Filed: Dec. 12, 1978

[30] Foreign Application Priority Data

Dec. 16, 1977 [JP] Japan ................................ 52-152248

[51] Int. Cl.³ ............................................ G01K 15/06
[52] U.S. Cl. ..................................... 250/576; 356/427
[58] Field of Search ............... 250/573, 574, 575, 576; 356/436, 440, 441, 244, 246, 427

[56] References Cited

U.S. PATENT DOCUMENTS

| | | |
|---|---|---|
| 3,555,284 | 1/1971 | Anderson . |
| 3,586,484 | 6/1971 | Anderson . |
| 3,771,878 | 11/1973 | Molloy et al. ........................ 356/427 |
| 4,055,076 | 10/1977 | Tropea ................................ 356/427 |

Primary Examiner—David C. Nelms
Attorney, Agent, or Firm—Lowe, King, Price & Becker

[57] ABSTRACT

A high density liquid is used to simultaneously transfer a liquid sample and a liquid reagent from antechambers formed in a centrifuge rotor to a transmissive measurement chamber formed in a radially outer region of the same rotor. The antechambers for the sample and the reagent and a reservoir chamber for the high density liquid are all elongated radially of the rotor and in fluidic connection through the radially outermost ends of the respective chambers. First the high density liquid is introduced into the antechambers so as to occupy a radially outer portion of each chamber, and then the sample and the reagent are introduced into the respective antechambers through their radially innermost ends. Thereafter the sample and the reagent are forced to flow out of the respective antechambers to enter the measurement chamber by additionally introducing the high density liquid into the reservoir chamber while the rotor is rotating.

9 Claims, 11 Drawing Figures

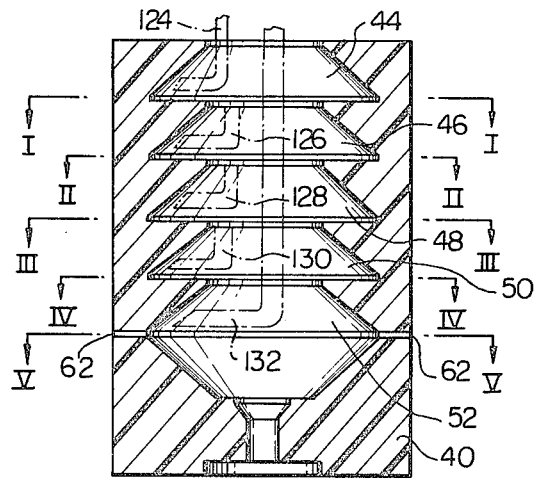
Fig. 3
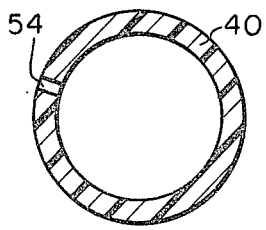
Fig. 4-(I)
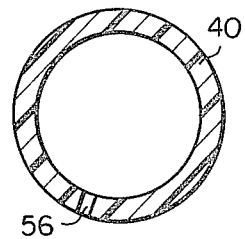
Fig. 4-(II)
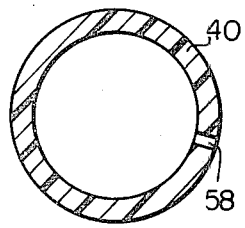
Fig. 4-(III)
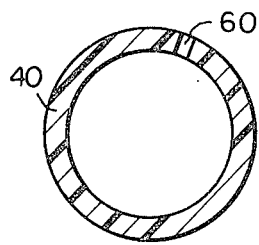
Fig. 4-(IV)
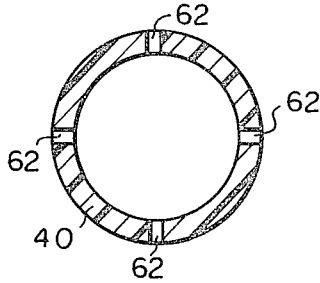
Fig. 4-(V)

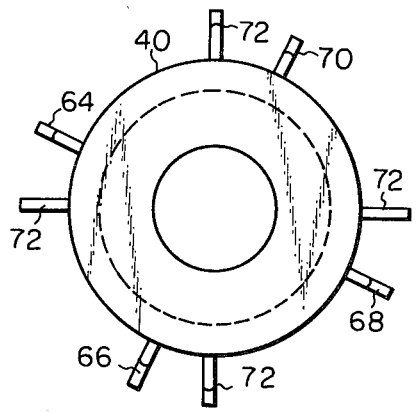
Fig. 5
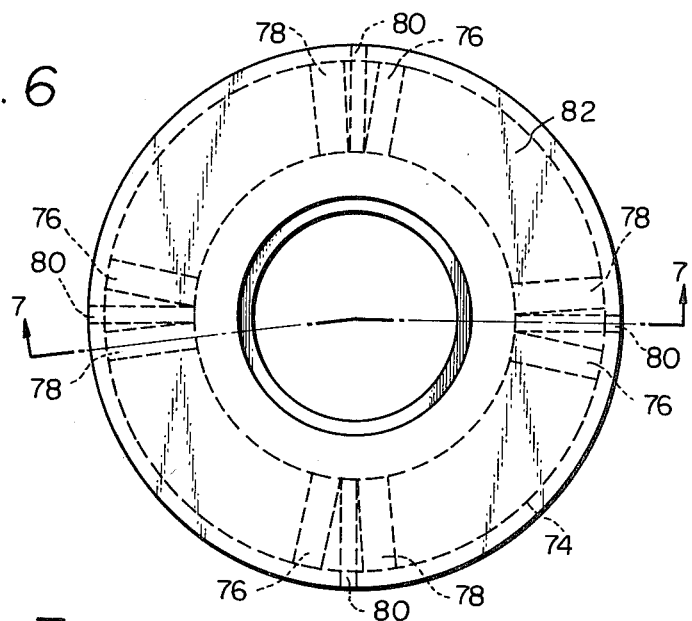
Fig. 6
Fig. 7
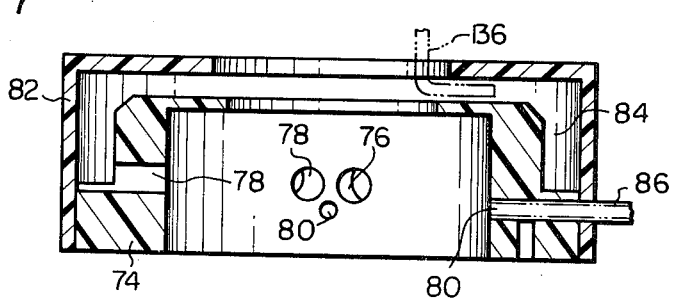

METHOD AND INSTRUMENT FOR PHOTOMETRIC ANALYSIS OF LIQUID USING CENTRIFUGE ROTOR

BACKGROUND OF THE INVENTION

This invention relates to a method of photometrically analyzing a liquid sample in a centrifuge rotor and an analytical instrument for performing the same method.

The application of photometry to a quantitative or qualitative analysis of a liquid mixture of a sample and a reagent is now quite familiar as represented by examination of human blood serum in the diagnosis of disease as well as for research purposes.

Also it is known to perform a photometrical analysis or examination of a liquid sample by utilizing a centrifuge rotor assembly in which the sample and a reagent are forced to flow into a chamber defined by transparent walls and mix therein by the action of centrifugal force. For example, U.S. Pat. Nos. 3,555,284 and 3,586,484 disclose photometric analyzers of this type. As an inconvenience to the users of such analyzers, cleaning of the interior of the centrifuge rotor after completion of a run, or a series of runs, of experiment (in preparation for a next experiment on a different kind of sample) needs to be performed by detaching the rotor from a drive motor portion of the instrument. Accordingly the cleaning operation requires much time and labor, and it is inevitable that the preceding and succeeding runs are performed with a considerably long interval of time.

As anoter inconvenience of an analyzer of the above described type when the liquid sample is a human blood serum, as an example, there is the need of preparing the sample by centrifugal separation of human blood into blood clots and serum by means of another centrifuge. This pretreatment takes considerable time and labor, and there arises a necessity for careful storage of the prepared serum samples which are liable to undergo changes in biochemical properties.

SUMMARY OF THE INVENTION

It is an object of the present invention to provide an improved method of photometrically analyzing a liquid sample mixed with a reagent in a centrifuge rotor, which method is free of the above described inconveniences of resembling conventional methods and can be performed easily and efficiently.

It is another object of the invention to provide an improved photometric analyzer of the type utilizing a centrifuge rotor, which analyzer is used for performing the method according to the invention and, in case of need, can serve the function of preparing a liquid sample by centrifugal separation immediately before analysis.

Fundamentally, a photometric analysis method according to the invention utilizes a centrifuge rotor which is formed with a sample chamber, a reagent chamber and a reservoir chamber each elongated and oriented radially of the rotor. These chambers are in fluidic connection such that the reservoir chamber communicates with both the sample chamber and the reagent chamber through the radially outermost ends of these three chambers. Furthermore, formed in a region radially outward from the sample chamber and the reagent chamber is a light-transmissive measurement chamber elongated and oriented radially of the rotor, and a passageway connects the measurement chamber to the radially innermost ends of the sample chamber and the reagent chamber. As a first step of analysis, a liquid which is higher in density than either of a sample liquid and a reagent liquid is introduced into both the sample chamber and the reagent chamber through the reservoir chamber so as to leave the sample chamber and the reagent chamber each partly vacant. Then the sample is introduced into the sample chamber through its radially innermost end and the reagent into the reagent chamber through its radially innermost end while the rotor is rotating. Thereafter, the high density liquid is further introduced into the sample chamber and the reagent chamber through the reservoir chamber while the rotor is rotating so as to force the sample and the reagent to flow out of the sample chamber and the reagent chamber, respectively, through the radially innermost ends of the respective chamber. Then the sample and the reagent are forced to enter the measurement chamber through the aforementioned passageway by the action of centrifugal force. A photometric analysis of the mixture of the sample and the reagent in the measurement chamber is conducted by projecting a light beam so as to intersect the measurement chamber and receiving the light beam transmitted through the measurement chamber by a photodetector means.

When the sample introduced into the sample chamber comprises a solid matter objectionable to the analysis, it is possible to centrifugally separate the solid matter from the sample by deferring the additional introduction of the high density liquid into the sample chamber and the reagent chamber for a while with continued rotation of the rotor. The additional introduction of the high density liquid after that causes only a supernatant portion of the sample to flow out of the sample chamber simultaneously with the outflow of the reagent from the reagent chamber.

Preferably, the rotor is formed with another reservoir chamber which communicates with the measurement chamber through the radially outermost end of the measurement chamber and a drain passageway connected to the aforementioned passageway for introduction of the sample and the reagent into the measurement chamber. Then it becomes possible to discharge the sample, reagent and their mixture entirely from the rotor while the rotor is rotating and at the same time wash the interior of the rotor with the high density liquid by introducing excess volumes of the high density liquid into the sample chamber, reagent chamber and the measurement chamber through the two reservoir chambers.

A fundamental construction of an analyzer according to the invention, too, will be understood from the above description about the analysis method.

BRIEF DESCRIPTION OF THE DRAWINGS

FIG. 3 is an enlarged sectional view of a part of the analyzer of FIG. 2;

FIGS. 4-(I) to 4-(V) are sectional views respectively taken along the lines I—I to V—V of FIG. 3;

FIG. 5 is a plan view of the part of FIG. 3, showing the connection of liquid feed pipes to this part;

FIG. 6 is a plan view of another part of the analyzer of FIG. 2; and

FIG. 7 is a sectional view taken along the line 7—7 of FIG. 6.

DESCRIPTION OF THE PREFERRED EMBODIMENTS

Figure 1:
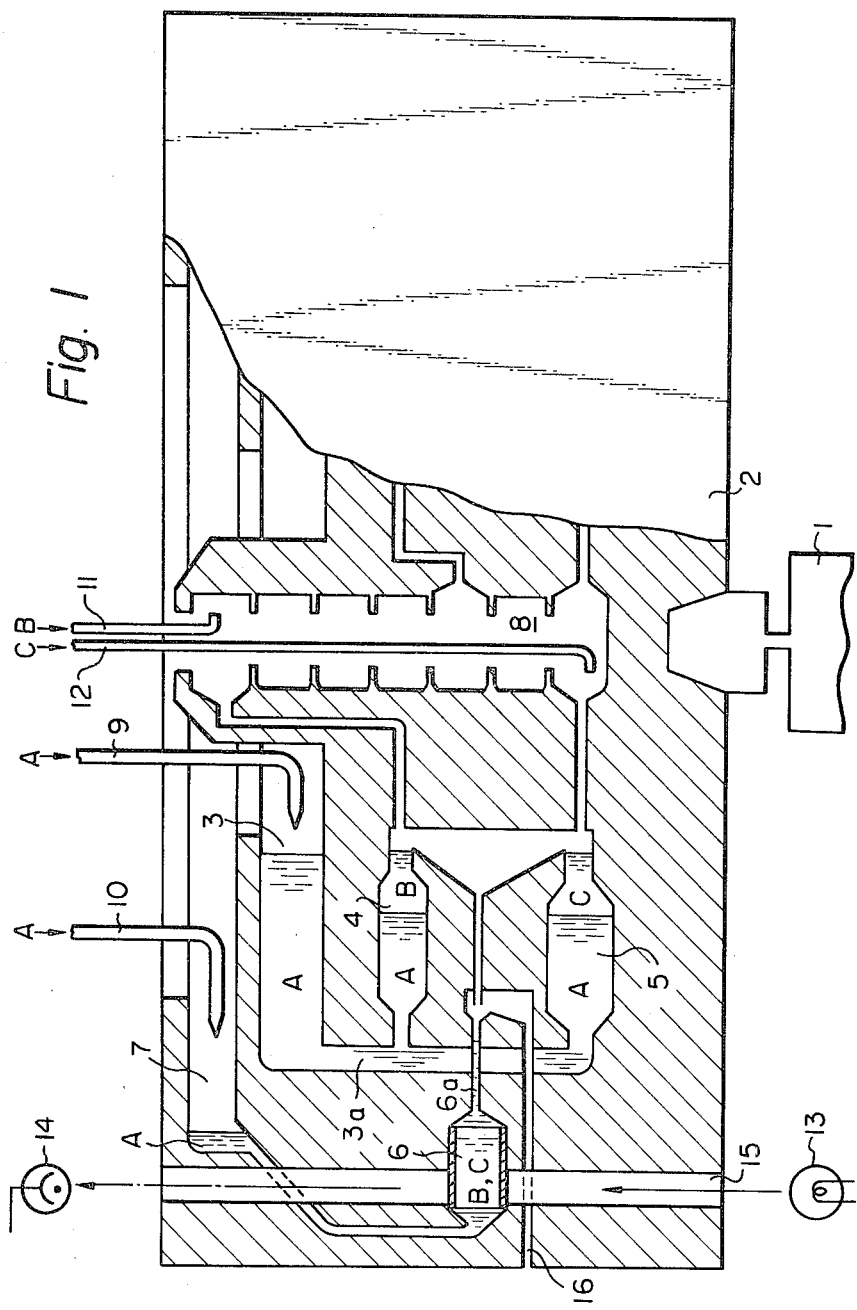
FIG. 1 shows in section a fundamental construction of an analyzer according to the invention.

To begin with, the principle of the invention will be described with reference to FIG. 1, wherein a rotor assembly in an analyzer according to the invention is illustrated simply as a single centrifuge rotor 2 formed with all the chambers and passageways essential to the analyzer. A drive motor 1 supports the rotor 2 to rotate it about a vertical axis. Formed in the rotor 2 are three cavities or chambers 3, 4 and 5 all elongated and oriented radially of the rotor 2, and a passageway 3a extends from the radially outermost end of the chamber 3 to the radially outermost ends of the other two chambers 4 and 5, so that these three chambers 3, 4 and 5 are in liquid communication with one another through this passageway 3a. At the radially innermost end the chamber 3 is open to the atmosphere such that a liquid A, which is higher in density than either of a sample liquid C to be examined or a liquid reagent B to be mixed with the sample C, can be introduced into the chamber 3 through a pipe 9. The two chambers 4 and 5 communicate with each other through the radially innermost ends thereof, and a distribution chamber 8 formed in a middle region of the rotor 2, i.e. radially inward from the chambers 3, 4 and 5, opens to the atmosphere at its upper end and communicates with the two chambers 4 and 5 through the radially innermost ends of these chambers 4 and 5 such that the reagent B and the sample C can be introduced respectively into the chamber 4 and the chamber 5 through a reagent feed pipe 11 and a sample feed pipe 12 inserted into the distribution chamber 8. The chamber 3 for the high density liquid A has the largest volume among the three chambers 3, 4 and 5. The reagent chamber 4 and the sample chamber 5 may be different in volume (i.e. in cross-sectional area) depending on the volume ratio of the reagent B to the sample C necessary to measurements.

In a region radially outward from the three chambers 3, 4 and 5, there is a measurement chamber 6 which also is elongated and oriented radially of the rotor 2, and a passageway 6a connects the radially innermost end of this chamber 6 with the radially innermost ends of the reagent chamber 4 and sample chamber 5. At the radially outermost end, the measurement chamber 6 communicates with another chamber 7, which opens to the atmosphere at its radially inward end such that the high density liquid A can be introduced into this chamber 7 through a feed pipe 10. A drain passageway 16 branches from the passageway 6a. The measurement chamber 6 is defined, at least partly, by a transparent tube inserted into the rotor 2, and the rotor 2 is bored parallel to the axis of rotation to give a through hole 15 which intersects the transparent tube portion of the measurement chamber 6. The analyzer comprises a light projecting means, represented by a lamp 13 in FIG. 1, on one side of the rotor 2 and a photodector means such as a photomultiplier tube 14 on the other side of the rotor 2 in such an arrangement that the photodetector 14 receives a light beam projected by the projecting means 13 and transmitted through the hole 15 (hence, across the measurement chamber 6) once a revolution of the rotor 2.

In operation, a high density liquid A, which is inactive to both the sample C and the reagent B, is introduced into the two reservoir chambers 3 and 7 respectively through the pipes 9 and 10 while the rotor 2 is rotated at a speed of, for example, about 500 r.p.m. An example of the high density liquid A is a 20% aqueous solution of sucrose. Due to centrifugal force created by the rotation of the rotor 2, the liquid A flows from the first reservoir chamber 3 into the reagent chamber 4 and the sample chamber 5 through the passageway 3a and, at the same time, from the second reservoir chamber 7 into the measurement chamber 6. The quantities of the liquid A introduced into the chambers 3 and 7 are controlled so as to leave a portion (a radially inward portion due to centrifugal force acting on the liquid A) of each of the reagent chamber 4 the sample chamber 5 and the measurement chamber 6 vacant. With continued rotation of the rotor 2, a liquid reagent B which is lower in density than the liquid A as exemplified by a pyrophosphate buffer solution (0.1 mole, pH:8.3) comprising nicotinamide dinucleotide ($10^{-3}$ mole) dissolved in pyruvate ($10^{-3}$ mole) is introduced into the reagent chamber 4 through the pipe 11 and the distribution chamber 8. The transfer of the reagent B from the distribution chamber 8 to the reagent chamber 4 occurs due to the centrifugal force. In the same manner, a liquid sample C such as a human blood serum (which also is lower in density than the liquid A) is introduced into the sample chamber 5 through the pipe 12 and the distribution chamber 8. Because of a difference in density and the action of the centrifugal force, the high density liquid A and the reagent B does not mix with each other in the reagent chamber 4 but assume a stratified state with the reagent B on the radially inward side. Similarly, the liquid A and the sample C in the sample chamber 5 are in two strata with the sample C on the radially inward side.

Then the high density liquid A is additionally introduced into the first reservoir chamber 3, and as a consequence into both the reagent chamber 4 and the sample chamber 5, in such a volume that a desired volume of the reagent B and a desired volume of the sampel C are forced to flow out of the chambers 4 and 5, respectively, through the radially innermost ends thereof. By the action of the centrifugal force, the reagent B and the sample C thus overflowed the chambers 4 and 5 flow into the measurement chamber 6 through the passageway 6a. The reagent B and the sample C undergoes mixing while they are passing through the passageway 6a and even after entrance into the measurement chamber 6.

Following the above described procedures, a photometric measurement or analysis of the sample C mixed with the reagent B in the measurement chamber 6 is conducted by utilizing the light projector 13 and the photodetector 14 while the rotor 2 is continuously rotated. The mixture B+C does not flow out of the measurement chamber 6 during measurement since the opening at the outermost end of this chamber 6 is blocked by the high density liquid A introduced from the reservoir chamber 7. For example, in the case of the sample C and the reagent B being a human blood serum and the aforementioned buffer solution, respectively, the absorbance of the mixture B+C to a light beam of 340 nm wavelength is measured to determine, for example, the enzyme activity of the lactic dehydrogenase in the blood serum from changes in the absorbance with the lapse of time.

After completion of a run of analysis, large volumes of the high density liquid A is introduced into the reservoir chambers 3 and 7 in the rotating rotor 2. Then, the reagent B retained in the chamber 4, the sample C retained in the chamber 5 and the mixture B+C in the measurement chamber 6 are forced to flow out of the respective chambers 4, 5 and 6 by the increased high density liquid A and are discharged from the rotor 2 through the drain passageway 16 by the action of the centrifugal force. The additional supply of a sufficiently large volume of the liquid A results in the discharge of a portion of the liquid A from the rotor 2 through the passageway 16 after the discharge of the reagent B, sample C and the mixture B+C. This means that the chambers 4, 5 and 6 and the passageways connected to these chambers are washed with the high density (inactive) liquid A. In preparation for a next run of analysis or measurement, an excess portion of the high density liquid A remaining in the rotor 2 can be recovered by inserting tip portions of the feed pipes 9 and 10 into the liquid A in the reservoir chambers 3 and 7 and connecting the pipes 9 and 10, for example, a suction pump.

As will be understood from the foregoing description, a primary feature of the invention resides in the use of the high density liquid A for discharge of the sample C and the reagent B respectively from the chambers 5 and 4. As an advantage of this method, the volumes of the sample C and the reagent B to be transferred respectively from the chambers 5 and 4 can be controlled readily and accurately by introducing a controlled volume of the high density liquid A into the first reservoir chamber 3 after the introduction of the sample C and the reagent B respectively into the chambers 5 and 4. Besides, the high density liquid A can be utilized for discharging the sample C, reagent B and the mixture B+C all from the rotor 2 at a desired opportunity and, at the same time, cleaning the chambers and passageways for the liquids B, C and B+C in the rotor 2. In practical applications, it is very convenient that the discharge of unnecessary liquids and cleaning of the interior of the rotor can be accomplished without need of stopping rotation of the rotor and detaching the rotor from the drive motor because of greatly reduced time and labor for the cleaning operation and the possibility of conducting a next run of measurement only with a very short interval of time.

When the sample C comprises a solid or semisolid component, the invention has a further advantage that the sample C can be subjected to centrifugal separation within the sample chamber 5 immediately before mixing with the reagent B. In the case of the sample C being a human blood by way of example, the introduction of the high density liquid A into the chambers 4 and 5 through the first reservoir chamber 3 after the admission of the reagent B and the sample (blood) C into these chambers 4, 5 is deferred for a while thereby to allow centrifugal separation of the blood C in the sample chamber 5 into blood clots (corpuscles) and serum. Then the blood serum alone can be discharged from the sample chamber 5 by the supply of the high density liquid A since the separated blood clots are higher in density than the blood serum and accordingly remain in a relatively outward (radially) region of the sample chamber 5. It is quite convenient that a sample comprising solid matter can be introduced into the analyzer without need of a centrifugal separation process as a pretreatment in a separate instrument, and it is favorable that the separation of the solid matter can be achieved within the analyzer immediately before photometric analysis since the separated liquid sample hardly undergoes changes in its properties before the analysis. Accordingly, it becomes unnecessary to carefully store changeful liquid samples such as human blood serum samples.

As will be illustrated hereinafter, an analyzer according to the invention may comprise two or more sets of the combination of the reagent chamber 4, sample chamber 5 and measurement chamber 6 (with all the measurement chambers 6 arranged circumferentially on the axis of rotation of the rotor 2) with a view to, for example, accomplishment of simultaneous measurements on a plurality of mixtures prepared by the addition of different kinds of reagents to the same sample liquid.

A preferred embodiment of an analyzer according to the invention will be described in detail with reference to FIGS. 2–7.

A centrifuge rotor in this instrument is not a single member but is an assembly of several members designed so as to be convenient for the provision of chambers and passageways in the rotor. Indicated at 20 is a drive motor with a shaft 22 extending vertically upwards. A generally disc-shaped rotor body 26 is horizontally mounted on the shaft 22 by means of a usual coupling 24, and a cylindrical distributor 40 is placed on the upper side of the rotor body 26 and is fixed to the upper end of the shaft 22 with a screw 42 such that an end portion of the distributor 40 fits into a shallow and circular recess 28 in a central region of the rotor body 26. The distributor 40 is formed with four reservoir chambers 44, 46, 48 and 50 for a reagent (or reagents) and another reservoir chamber 52 for a sample all in a vertical alignment on the axis of rotation. As shown in FIGS. 3–5, these chambers 44–52 are all circular in cross section, and pipes 64, 66, 68, 70 and 72 are connected respectively to these chambers 44–52 through radial holes 54, 56, 58, 60 and 62 in the cylindrical wall of the distributor 40. A centrifugal cylinder 74 is fixed to the rotor body 26 with screws 34 so as to concentrically surround the distributor 40. As shown in FIGS. 6 and 7, the centrifugal cylinder 74 is formed with four reagent chambers 76, four sample chambers 78 and four mixing chambers 80 each as radial holes through the wall of the cylinder 74 arranged such that one reagent chamber 76, one sample chamber 78 and one mixing chamber 80 makes a set and that the four sets of chambers are located circumferentially at equal intervals. The pipes 64, 66, 68 and 70 are connected respectively to the four reagent chambers 76, and the pipe 72 to the sample chambers 78. A cylindrical cover 82 is fixed to a flanged lower portion of the centrifugal cylinder 74 so as to concentrically surround the cylinder 74 and define a space 84, which serves as a reservoir chamber for a high density liquid, around and above the cylinder 74. Accordingly the radially outermost ends of the reagent chambers 76 and the sample chambers 78 are open to the high density liquid chamber 84. The radially outermost ends of the mixing chambers 80 do not open to the high density liquid chamber 84, and a pipe 86 is fitted into each of the mixing chambers 82 through the wall of the cylinder cover 82.

An annular recess 30 is formed in an outer region of the rotor body 26 with a distance between the cylinder cover 82 and inner periphery of the recess 30. Utilizing this recess 30, a ring 88 is fixed to the rotor body 26 with screws 36 so as to surround a lower portion of the cylinder cover 82, and a ring cover 90 is fitted into an annular gap between the outer periphery of the ring 88 and the outer periphery of the recess 30. The ring 88 is formed with four radial holes 92 in such an arrangement that the outer ends of the aforementioned pipes 86 face the radially inner ends of the four holes 92, respectively. The radially outer ends of the radial holes 92 are open to a space 98 defined between the ring 88 and the ring cover 90 to serve as a second reservoir chamber for the high density liquid. In addition, four radial holes 94 are formed through the ring 88 and the ring cover 90 as drain holes for the respective measurement chambers provided in the holes 92 as described below. Four vertical holes 96 are bored through the ring 88 so as to perpendicularly intersect the four radial holes 92, respectively, and four vertical holes 32 are bored through the rotor body 26 respectively in axial alignment with the holes 96. A transparent tube 100, for example, of glass is fitted into each of the four radial holes 92 with the provision of an O-ring 102 to utilize the interior of each tube 100 as a measurement chamber 101 of this analyzer. A drain pipe 104 is inserted into each of the radial holes 94 so as to open at its inner end to the space between the ring 88 and the cylinder cover 82 at a location close to the inner end of each of the transparent tubes 100 and in its outer end portion protrude radially outwardly from the ring cover 90. An eyepiece 106 is inserted into an upper portion of each of the four vertical holes 96 through a vertical hole (no numeral) in the ring cover 90 with the provision of O-rings 108.

A cup-shaped case 116 is mounted on the frame of the drive motor 20, and a cylindrical support 118 is fixed to the bottom of the case 116 so as to surround the rotor assembly of the above described construction. A lid or cover plate 120 is fixed to the uper end of the support 118 with screws 122. A light projector 110 is mounted on the outside of the cover plate 120 at such a location that a light beam can transmit from the projector 110 to a photodetector 112, which is placed on a holder 146 fixed to the inside of the case 116, through an aperture 121 in the cover plate 120, eyepiece 106, transparent tube 100 (measurement chamber 101), hole 96 and hole 32. The cover plate 120 has an aperture (no numeral) in its central region, and a holder 134 is fitted into this aperture to support pipes 124, 126, 128 and 130 to introduce four kinds of reagents respectively into the four chambers 44, 46, 48 and 50 in the distributor 40 and a pipe 132 to introduce a sample into the chambers 52. A pipe 136 extends through an aperture (no numeral) in the cover plate 120 to introduce a high density liquid into the first reservoir chamber 84 and is rotatably supported by a holder 140 attached to the cover plate 120. Another pipe 138 to introduce the high density liquid into the second reservoir chamber 98 is similarly (rotatably) supported by a holder 142. An annular saucer 114 is attached to the inside of the cylindrical support 118 so as to receive a liquid discharged from the rotor assembly through the drain pipes 104. In the illustrated embodiment, a lid 150 for the upper opening of the case 116 is a swing board like a door supported by hinges 148.

Figure 2:
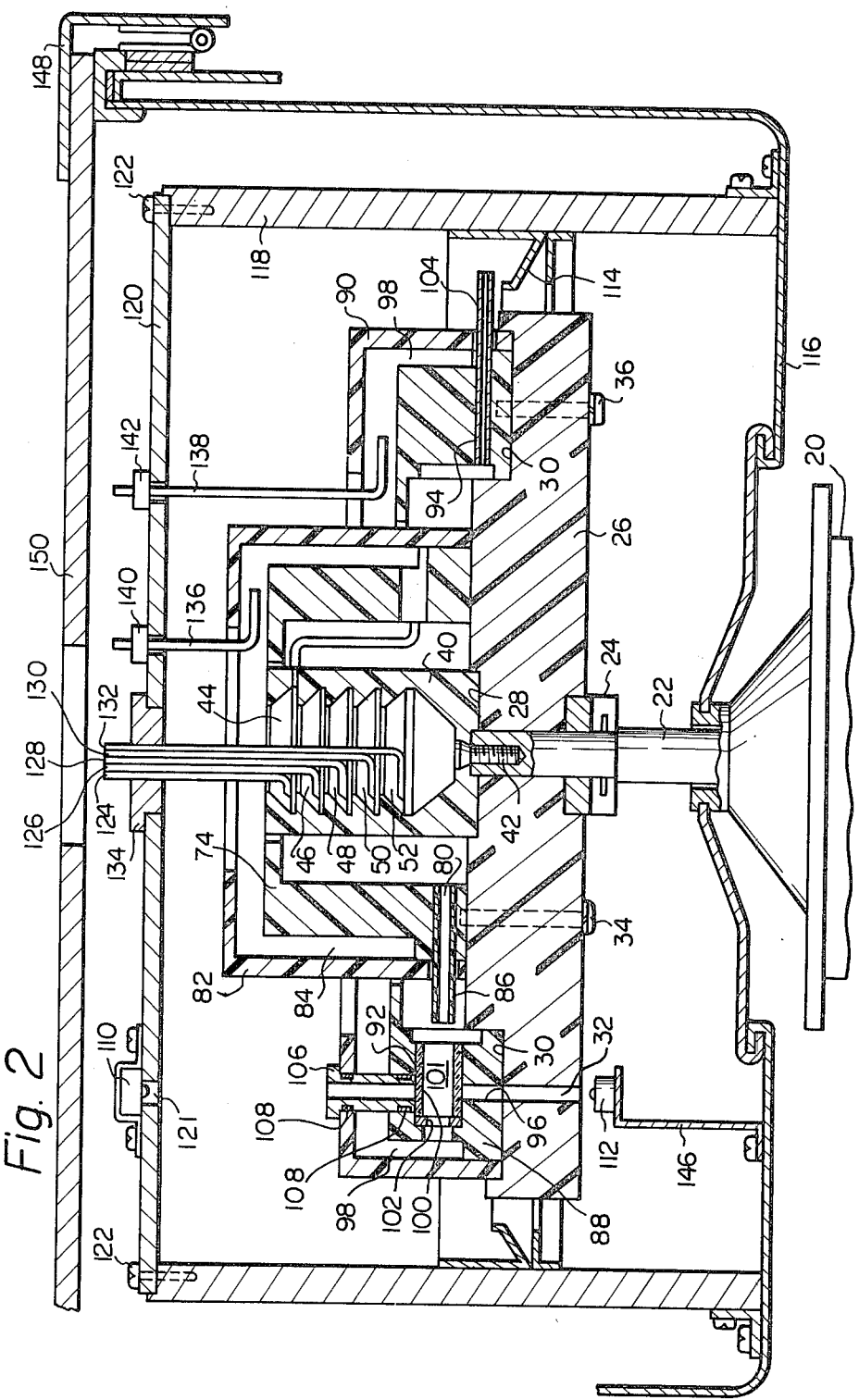
FIG. 2 is a sectional view of an analyzer as an embodiment of the invention.

The operation of the analyzer of FIG. 2 will be understood from the foregoing description with reference to FIG. 1. The sample and the reagents are forced to flow out of the sample chambers 78 and the reagent chambers 76 by introducing an additional quantity of the high density liquid into the first reservoir chamber 84 while the rotor assembly is rotating, and the sample and the respective reagents enter the mixing chambers 80, and then the resulting mixtures enter the measurement chambers 101, by the action of centrifugal force. Discharge of the liquid from the rotor assembly through the drain pipes 104 can be accomplished by utilizing the second reservoir chamber 98 as well as the chamber 84 to supply a sufficient volume of the high density liquid to the rotating rotor assembly.

What is claimed is:

1. A method of photometrically analyzing a liquid mixture of a sample and a reagent, comprising the steps of:
    (a) forming in a centrifuge rotor a sample chamber, a reagent chamber and a reservoir chamber each elongated and oriented radially of said rotor in such a fluidic connection that said reservoir chamber communicates with both said sample chamber and said reagent chamber through the radially outermost ends thereof;
    (b) forming in said rotor a light-transmissive measurement chamber which is elongated, oriented radially of said rotor and located radially outward from said sample chamber and said reagent chamber and a passageway which connects said measurement chamber to the radially innermost ends of said sample chamber and said reagent chamber;
    (c) introducing a high density liquid which is higher in density than either of said sample and said reagent into both said sample chamber and said reagent chamber through said reservoir chamber so as to leave said sample chamber and said reagent chamber each partly vacant;
    (d) introducing a liquid sample into said sample chamber through the radially innermost end thereof and introducing a liquid reagent into said reagent chamber through the radially innermost end thereof while said rotor is rotating;
    (e) further introducing said high density liquid into both said sample chamber and said reagent chamber through said reservoir chamber, while said rotor is rotating, so as to force said sample and said reagent to flow out of said sample chamber and said reagent chamber, respectively, through the radially innermost ends of the respective chambers, whereby said sample and said reagent enter said measurement chamber through said passageway by the action of centrifugal force; and
    (f) projecting a light beam so as to intersect said measurement chamber and receiving and analyzing the light beam transmitted through said measurement chamber, in which is contained a mixture of said sample and said reagent.

2. A method according to claim 1, further comprising the step (g) of continuing the rotation of said rotor for a predetermined period of time between the steps (d) and (e) so that said sample undergoes centrifugal separation within said sample chamber, the volume of said high density liquid introduced in the step (e) being controlled such that only a supernatant portion of said sample is forced to flow out of said sample chamber.

3. A method according to claim 1 or 2, further comprising the step (h) of introducing said high density liquid into said measurement chamber through the radially outermost end thereof, the quantity of said high density liquid introduced in the step (h) being controlled so as to block outflow of said mixture from said measurement chamber through the radially outermost end thereof during the steps (e) and (f) and to discharge and wash away said mixture from said measurement chamber after the step (f).

4. A method according to claim 3, further comprising the step of additionally introducing said high density liquid into both said sample chamber and said reagent chamber through said reservoir chamber after the step (f) thereby to discharge and wash away said sample and said reagent from said sample chamber and said reagent chamber, respectively.

5. A method according to claim 1 or 2, further comprising the steps of forming in said rotor at least one additional combination of another sample chamber, another reagent chamber, another passageway and another measurement chamber substantially identically with the combination of said sample chamber, said reagent chamber, said passageway and said measurement chamber formed in the steps (a) and (b), said reservoir chamber being made to communicate also with said another sample chamber and said another reagent chamber through the radially outermost ends thereof; and introducing an each different reagent into said another reagent chamber of each of said at least one additional combination substantially simultaneously with the step (d), whereby in the step (e) an each different reagent enters said another measurement chamber of each of said at least one additional combination together with said sample.

6. An instrument for photometric analysis of a liquid mixture of a sample and a reagent, comprising:
   a centrifuge rotor which is formed with a sample chamber, a reagent chamber and a high density liquid reservoir chamber each elongated and oriented radially of said rotor in such a fluidic connection that said reservoir chamber communicates with both said sample chamber and said reagent chamber through the radially outermost ends thereof, said rotor being further formed with a light-transmissive measurement chamber which is elongated, oriented radially of said rotor and located radially outward from said sample chamber and said reagent chamber, and a passageway which connects said measurement chamber to the radially innermost ends of said sample chamber and said reagent chamber;
   first liquid feed means for introducing a high density liquid into said reservoir chamber and, as a consequence, also into said sample chamber and said reagent chamber through the radially outermost ends thereof;
   second liquid feed means for introducing a liquid sample into said sample chamber through the radially innermost end thereof;
   third liquid feed means for introducing a liquid reagent into said reagent chamber through the radially innermost end thereof;
   drive means for supporting and rotating said centrifuge rotor; and
   photometrical means for projecting a light beam so as to intersect said measurement chamber and receiving and analyzing the light beam transmitted through said measurement chamber.

7. An instrument according to claim 6, wherein said rotor is further formed with another reservoir chamber which communicates with said measurement chamber through the radially outermost end of said measurement chamber, the instrument further comprising means for introducing said high density liquid into said another reservoir chamber and, as a consequence, also into said measurement chamber.

8. An instrument according to claim 7, wherein said rotor has a drain passageway through which liquids can flow from said sample chamber, said reagent chamber and said measurement chamber to the exterior of said rotor when a large volume of a liquid is introduced into said reservoir chamber and said another reservoir chamber.

9. An instrument according to any of claims 6 to 8, wherein said rotor has at least one additional combination of another sample chamber, another reagent chamber and another light-transmissive measurement chamber each elongated and oriented radially of said rotor and respectively arranged and connected identically with said sample chamber, said reagent chamber and said measurement chamber, said rotor being formed with another passageway for each of said at least one additional combination to connect said another measurement chamber to the radially innermost ends of said another sample chamber and said another reagent chamber, the instrument further comprising means for introducing said sample into said another sample chamber of each of said at least one additional combination and means for introducing an each different liquid reagent into said another reagent chamber of each of said at least one additional combination.

* * * * *